United States Patent [19]

Dawe

[11] Patent Number: 4,933,462

[45] Date of Patent: Jun. 12, 1990

[54] SYNTHESIS OF 3-(2-HYDROXYETHYL)-2-OXAZOLIDINONES

[75] Inventor: Robert D. Dawe, Fort Saskatchewan, Canada

[73] Assignee: The Dow Chemical Company, Midland, Mich.

[21] Appl. No.: 223,582

[22] Filed: Jul. 25, 1988

[51] Int. Cl.$^5$ .......................................... C07D 263/38
[52] U.S. Cl. .................................... 548/229; 548/231
[58] Field of Search ................................ 548/229, 231

[56] References Cited

U.S. PATENT DOCUMENTS

| | | | |
|---|---|---|---|
| 2,399,118 | 2/1942 | Homeyer | 548/229 |
| 2,437,390 | 3/1948 | Homeyer | 260/307 |
| 2,755,286 | 7/1956 | Bell, Jr. et al. | 260/307 |
| 2,865,926 | 12/1958 | Harrington, Jr. | 260/307 |
| 3,168,525 | 2/1965 | Baizer | 260/307 |
| 4,209,628 | 6/1980 | Ikeda et al. | 548/229 |
| 4,500,717 | 2/1985 | Cook et al. | 548/229 |

OTHER PUBLICATIONS

Drechsel, CA, 1958, #2837d.
"Sanyo (I)", CA 102:166734, Dec. '84.
Katritzky "Heterocyclic Chemistry", v. 6, Part 4B, pp. 229–230, 1984.
Derwent Abstract of JP 8605286708, "Sanyo (I)", 6/84.
CA of JP 59222481.

*Primary Examiner*—Johnnie R. Brown
*Assistant Examiner*—Frederick F. Tsung
*Attorney, Agent, or Firm*—Paula Sanders Ruhr

[57] ABSTRACT

A 3-(substituted)-2-oxazolidinone is prepared by refluxing equimolar proportions of a dialkanolamine and dimethyl carbonate in the absence of a catalyst. A yield of at least about 90 percent of a highly pure product is obtained.

1 Claim, No Drawings

SYNTHESIS OF 3-(2-HYDROXYETHYL)-2-OXAZOLIDINONES

BACKGROUND OF THE INVENTION

This invention is related to processes for the preparation of 3-(substituted)-2-oxazolidinones, particularly 3-(2-hydroxyethyl)-2-oxazolidinone.

The 2-oxazolidinone compounds are known compounds and are useful for various purposes such as precursors for surfactants. Various methods for their production are known. For example, U.S. Pat. No. 2,437,390 teaches that 2-oxazolidinones may be prepared by reacting a $\beta$-amino alcohol and an alkyl carbonate under anhydrous conditions and typically in the presence of a catalyst. Another approach is taught in U.S. Pat. No. 3,168,525 where it is disclosed to prepare certain 2-oxazolidinones by acylating a 1-halo-2-carbamyl-oxy-3-substituted propane and cyclizing the resulting propane. U.S. Pat. No. 4,500,717 teaches that 2-oxazolidinones may be prepared by the reaction of a 2-hydroxyalkyl carbonate with an alkylene oxide or alkylene carbonate in the presence of a catalyst. U.S. Pat. No. 4,209,628 teaches that 2-oxazolidinones are prepared by the reaction of carbon dioxide with an aziridine compound preferably in the presence of a Lewis acid catalyst.

None of these processes for the preparation of oxazolidinones are without problems. The existing problems include low yields; the need to continuously distill by-products from the reaction mixture to force the reaction to completion: the production of a low purity product requiring purification steps and the requirement for the use of catalysts. Thus, what is needed is a simple, efficient process for the preparation of 2-oxazolidinones that results in a high yield of product having high purity.

SUMMARY OF THE INVENTION

The present invention is such a process for the preparation of 3-(substituted)-2-oxazolidinones comprising contacting dimethyl carbonate and a $\beta$-amino alcohol in the absence of a catalyst and heating the mixture to reflux temperatures and maintaining the mixture at reflux for a sufficient time and under conditions necessary to form the 3-(substituted)-2-oxazolidinone in a yield of at least about 90 percent based on the reactant present in the smaller molar amount.

The 2-oxazolidinones produced by the process of this invention are useful as intermediates in the preparation of drugs and polymers. For example, the 2-oxazolidinones are useful as intermediates in the production of fibers, tablet coatings, lubricant additives, rust inhibitors and dyeing assistants.

It is surprising that the process of this invention results in a high yield of 2-oxazolidinones with high purity without the use of a catalyst or harsh reaction conditions.

DETAILED DESCRIPTION OF ILLUSTRATIVE EMBODIMENTS

The reactants useful in the process of this invention are dimethyl carbonate and $\beta$-amino alcohols. The $\beta$-amino alcohols are preferably dialkanolamines corresponding to the formula $R^1R^2NH$ wherein $R^1$ and $R^2$ are separately in each occurrence lower alkoxy such as methoxy, ethoxy or propoxy with the proviso that at least one of $R^1$ and $R^2$ is ethoxy It is preferred that $R^1$ and $R^2$ are each ethoxy and thus the most preferred $\beta$-amino alcohol is diethanolamine.

The dimethyl carbonate and $\beta$-amino alcohol may be used in any molar proportions under which the 2-oxazolidinone will be formed under the conditions of this invention. It is preferred to use approximately equimolar proportions of the reactants.

The temperatures useful in the practice of this invention are those at which the reactants reflux. In a preferred embodiment where the reactants are dimethyl carbonate and diethanolamine, it is preferred to heat the mixture to 90° C., the temperature at which the mixture begins to reflux. The temperature then drops to about 64° C. as the reactants continue to reflux until the reaction is complete. The time required for the reaction to reach completion is typically about 12 hours. When the reaction is halted at shorter times, the yield is decreased. Longer reaction times result in no advantage. The reaction may be conducted at superatmospheric or subatmospheric pressure but is preferably conducted at about atmospheric pressure.

The reaction is advantageously conducted in the absence of a solvent although a solvent may be used if desired. The reaction is conducted in the presence of air and anhydrous conditions are not required.

The yield of 2-oxazolidinone obtained by the practice of this invention is preferably at least about 90 percent, more preferably at least about 95 percent. The yield is most preferably at least about 99 percent. The yield is determined by considering the amount of reactants converted to the desired product.

In a preferred embodiment of this invention, equimolar amounts of dimethyl carbonate and diethanolamine are mixed and heated to reflux. The mixture is maintained at reflux until essentially all of the reactants are consumed as measured by gas chromatography. The product mixture consists of methanol and 3-(2-hydroxyethyl)-2-oxazolidinone. The methanol is removed by distillation leaving essentially pure 3-(2-hydroxyethyl)-2-oxazolidinone as confirmed by gas chromatography.

The following example is presented to illustrate the invention and should not be interpreted as limiting it in any way. Unless stated otherwise, all parts and percentages are given by weight.

Example - Preparation of 3-(hydroxyethyl)-2-oxazolidinone

Diethanolamine (105.0 g, 1.00 mole) and dimethyl carbonate (90.0 g, 1.00 mole) are placed in a reaction vessel equipped with a reflux condenser. The two materials are immiscible at ambient temperature (22° C.). The mixture is then heated to 90° C. At this temperature, the solution becomes homogeneous and reflux begins. The temperature of the vapor decreases to 64° C. after several minutes of reflux and remains at this temperature. The reaction is complete after 12 hours as determined by gas chromatography. Methanol is removed from the product mixture under reduced pressure. The remaining product is 129.8 g of 3-(hydroxyethyl)-2-oxazolidinone, identified by $^{13}C$ NMR, which represents a yield of 99 percent. The product's purity is confirmed by gas chromatography which detects no impurities.

What is claimed is:

1. A process for the preparation of 3-(2-hydroxyethyl)-2-oxazolidinone comprising contacting, in the absence of anhydrous conditions, equimolar portions of dimethyl carbonate and diethanolamine in the absence of a catalyst; heating the mixture to reflux at 90° C.; maintaining the mixture at reflux for about 12 hours; distilling off methanol and recovering the essentially pure 3-(2-hydroxyethyl)-2-oxazolidinone in a yield of at least about 90 percent.

* * * * *